(12) United States Patent
Oki et al.

(10) Patent No.: US 6,554,817 B1
(45) Date of Patent: Apr. 29, 2003

(54) DEVICE FOR DISPOSING EXCREMENT

(75) Inventors: Nobuyoshi Oki; Syuei Tamura; Hiroshi Sakai; Kimio Sato, all of Tokyo (JP)

(73) Assignee: Niles Parts Co., Ltd. (JP)

( * ) Notice: Subject to any disclaimer, the term of this patent is extended or adjusted under 35 U.S.C. 154(b) by 32 days.

(21) Appl. No.: 09/686,139

(22) Filed: Oct. 11, 2000

(30) Foreign Application Priority Data

Oct. 18, 1999 (JP) .......................................... 11-295988

(51) Int. Cl.[7] ................................................. A61F 13/15
(52) U.S. Cl. ...................... 604/393; 604/355; 604/327; 604/334; 4/455; 4/456
(58) Field of Search ............................... 604/355, 327, 604/334, 393; 4/616, 443–456

(56) References Cited

U.S. PATENT DOCUMENTS

| 3,574,239 A | * | 4/1971 | Sollerud .............................. 4/1 |
| 3,783,473 A | * | 1/1974 | Engquist ....................... 15/322 |
| 5,681,297 A | * | 10/1997 | Hashimoto et al. ......... 604/355 |
| 5,941,859 A | * | 8/1999 | Lerman ....................... 604/289 |
| 6,167,578 B1 | * | 1/2001 | Kitamura ...................... 4/443 |

FOREIGN PATENT DOCUMENTS

| JP | 3-166282 | 6/1991 |
| JP | 4-364841 | 12/1992 |

* cited by examiner

Primary Examiner—John G. Weiss
Assistant Examiner—Jacqueline F Stephens
(74) Attorney, Agent, or Firm—Rader, Fishman & Grauer PLLC; Ronald P. Kananen, Esq.

(57) ABSTRACT

A device for disposing excrement is provided which can feed air to an interior of a diaper cup main body 2. The diaper cup main body 2 forms a space A as a passage for feeding the air from an air feed hose to air blow ports 2e, 2f, 2g of the diaper cup main body. The space A is formed by joining together an upper cup 2a and a lower cup 2b. The upper cup 2a is adapted to be placed on a pelvic region of a human body and has the air blow ports 2e, 2f, 2g. The lower cup 2b has a connecting cylinder portion 2i to be connected to a wash-water feed hose 17, a connecting cylinder portion 2h to be connected to an excrement suction hose 16, and a connecting cylindrical portion 2j to be connected to an air feed hose 18.

14 Claims, 12 Drawing Sheets

DEVICE FOR DISPOSING EXCREMENT

BACKGROUND OF THE INVENTION

1. Field of the Invention

The present invention relates to devices for disposing excrement of sick persons unable to walk, aged bedridden in hospitals, and the like. More particularly, the present invention relates to a device for disposing excrement which is capable of automatically disposing of the excrement of a sick or bedridden person and washing the places tainted with the excrement.

2. Description of the Related Art

A conventional device for disposing excrement is disclosed, for example, in Japanese Patent Laid-Open No. 364841/1992. The conventional device for disposing excrement has, in a center of a diaper cover, a hole opened to insert through an evacuation pipe to discharge excrement, a pipe to feed warm water, a pipe to feed warm air, and a cord connected to a sensor to detect excrement.

However, the conventional device for disposing excrement is restricted in flexibility, despite adopting a soft insulative material. Due to the difficulty in matching to various body forms, the conventional device sometimes fails to provide a close fit with the wearer's pelvic region, thereby resulting in wash water or excrement leaking from around the diaper cup.

The conventional device also has a problem in that a human body will sometimes block an outlet port for ejecting air to dry an inside of the diaper cup moistened with wash water or the like, thereby not allowing air to enter into the diaper cup.

SUMMARY OF THE INVENTION

An object of the present invention is to solve the problems in the conventional device for disposing excrement described above. More specifically, it is an object of the invention to provide a device for disposing excrement which conforms to various human body shapes and sizes, and which can efficiently eject dried air toward the discharge port into a diaper cup moistened with wash water or the like, thereby discharging excrement left in the diaper cup.

The present invention has been made in order to solve the above-stated problems in the related art. The present invention provides a device for disposing excrement, comprising: a diaper cup main body for enclosing a pelvic region of a human body; a wash-water feed hose connected to the diaper cup main body for feeding wash water into an interior thereof; an excrement suction hose connected to the diaper cup main body for sucking the wash water and excrement in the interior; and an air feed hose connected to the diaper cup main body for feeding air to the inside. The device for disposing excrement is characterized by the diaper cup main body forming a space as a passage to feed air from the air feed hose to an air blow port of the diaper cup main body by joining an upper cup arranged on a side of a pelvic region of a human body and a lower cup matched to the upper cup.

The upper cup preferably has a connecting cylinder portion to be connected to the excrement suction hose and the air blow port, and the lower cup has a connecting portion for installing the wash-water feed hose and a connecting cylinder portion to be connected to the air feed hose.

The diaper cup main body is preferably arranged with a water feed pipe and a cord within the space of the diaper cup main body. The water feed pipe is connected to a private-parts wash nozzle and an anus wash nozzle installed in the upper cup, and the cord is connected to a feces-detecting sensor and a urine-detecting sensor installed in the upper cup.

The upper cup of the diaper cup main body preferably has a cavity and an inner wall. The cavity provides a non-contact state with a human body and is formed in a surface of the upper cup on a side to be fit on a pelvic region of a human body. The space is formed on a side of the upper cup opposite from the cavity. The inner wall is formed to join the lower cup. The air blow port is formed at plurality of positions in an upper end of the cavity.

The upper cup of the diaper cup main body is preferably formed with the air blow port in an upper end center of the cavity. The air blow port is formed with a guide wall to converge air flowing through the space.

The diaper cup main body preferably has a flap covering the air blow port on a side of the diaper cup main body to be fit on a pelvic region of a human body.

The diaper cup main body is preferably formed arcuate in the upper end of the cavity, and the flap is formed generally arcuate and matched to a shape of the upper end of the cavity. The flap is fixed at a plurality of positions to thereby form an outlet port communicating to the air blow port.

The flap is preferably arranged in a slant surface of the upper end of the cavity of the diaper cup main body and screwed to the diaper cup main body in a side portion of the air blow port.

The diaper cup main body is preferably continuously arranged with a waist-fit seat in the upper end, and the waist-fit seat has a support portion provided on the flap.

The waist-fit seat preferably has a plate-like portion to be inserted in a bag provided in a changeable diaper, and a slant portion provided between the plate-like portion and the support portion and formed with a cutout groove.

The upper cup and the lower cup of the diaper cup main body are preferably formed of a hard resin, and the flap and the waist-fit seat are formed of a resin that is softer than the upper cup and the lower cup and easy to bend and deform.

The diaper cup main body preferably has a cup-washing nozzle on an inner side of the flap in the vicinity of the air blow port to flow away excrement excreted by a sick person or the like.

DETAILED DESCRIPTION OF THE PREFERRED EMBODIMENTS

Preferred embodiments of the present invention will now be explained in detail with reference to FIGS. 1 to 20 of the drawings.

Figure 1:
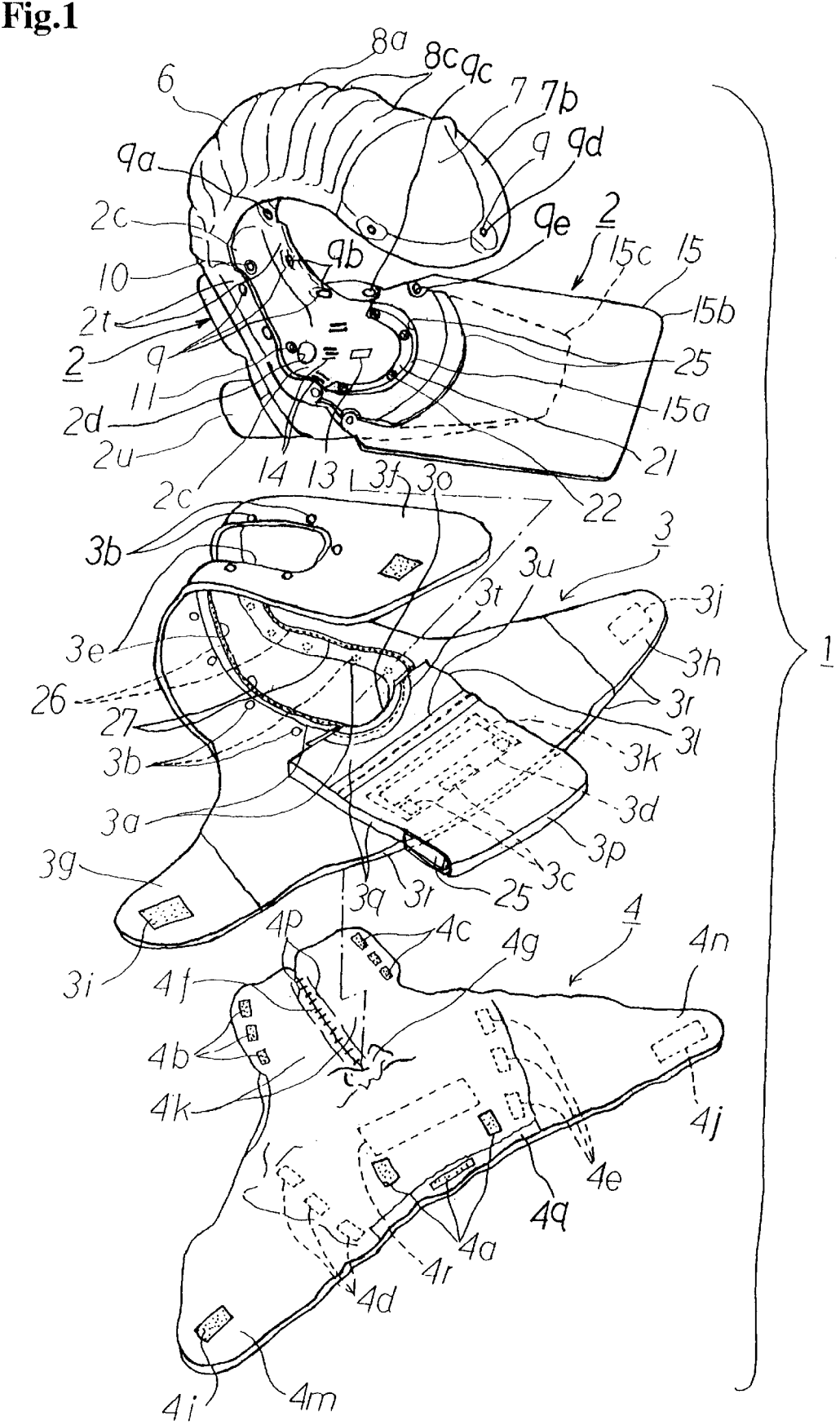
FIG. 1 is a perspective view showing a device for disposing excrement according to an embodiment of the present invention.
Figure 2:
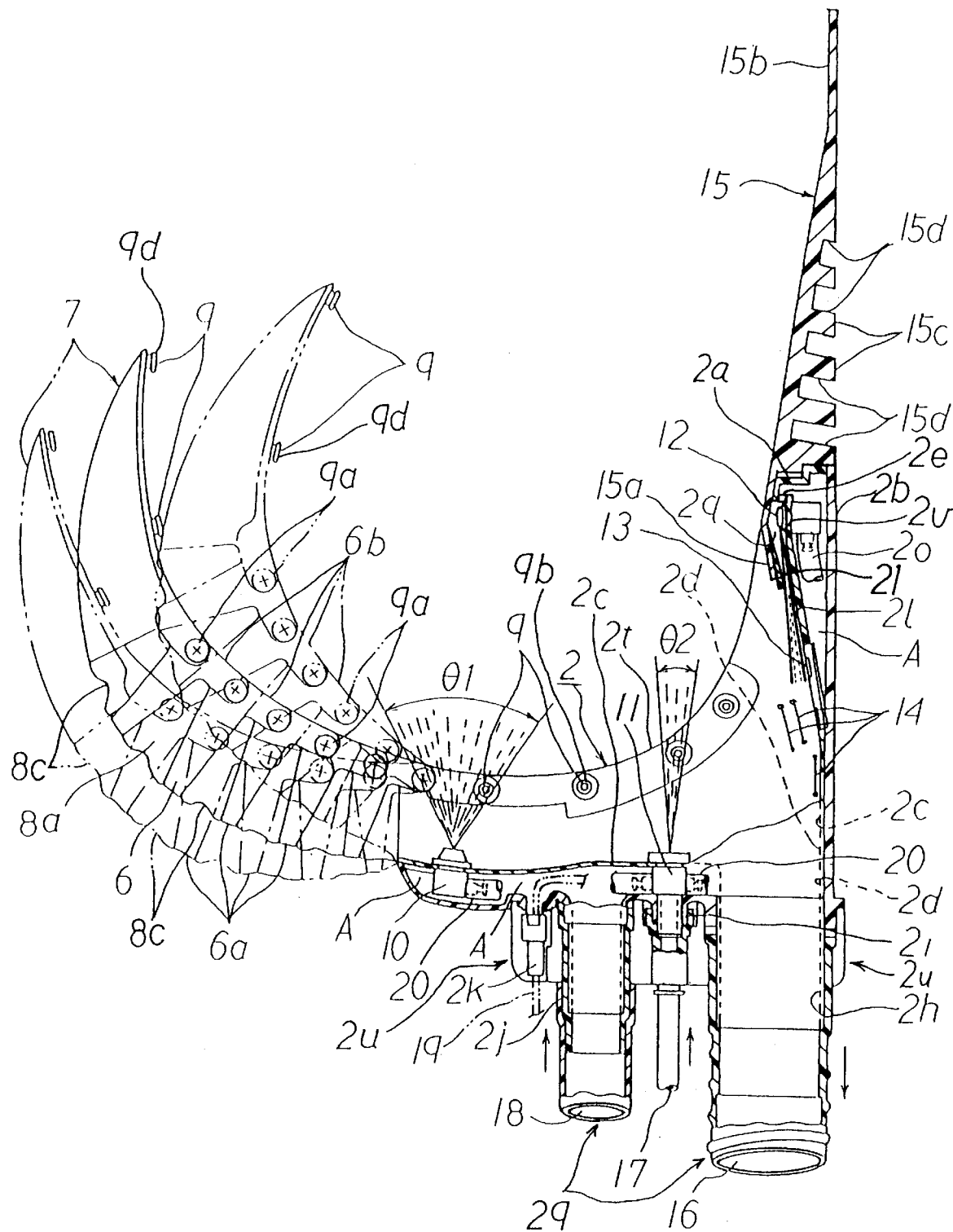
FIG. 2 is a magnified center lengthwise sectional view of a diaper cup main body of the invention.

As shown in FIG. 1, a diaper cup unit 1 comprises a diaper cup main body 2, a changeable diaper 3, and a diaper cover 4. The diaper main body 2, for enclosing a pelvic region of a human body as shown in FIG. 2, is provided continuous with a plurality of concertina joints 6 to have a front cover 7 structured for free bending.

Figure 5:
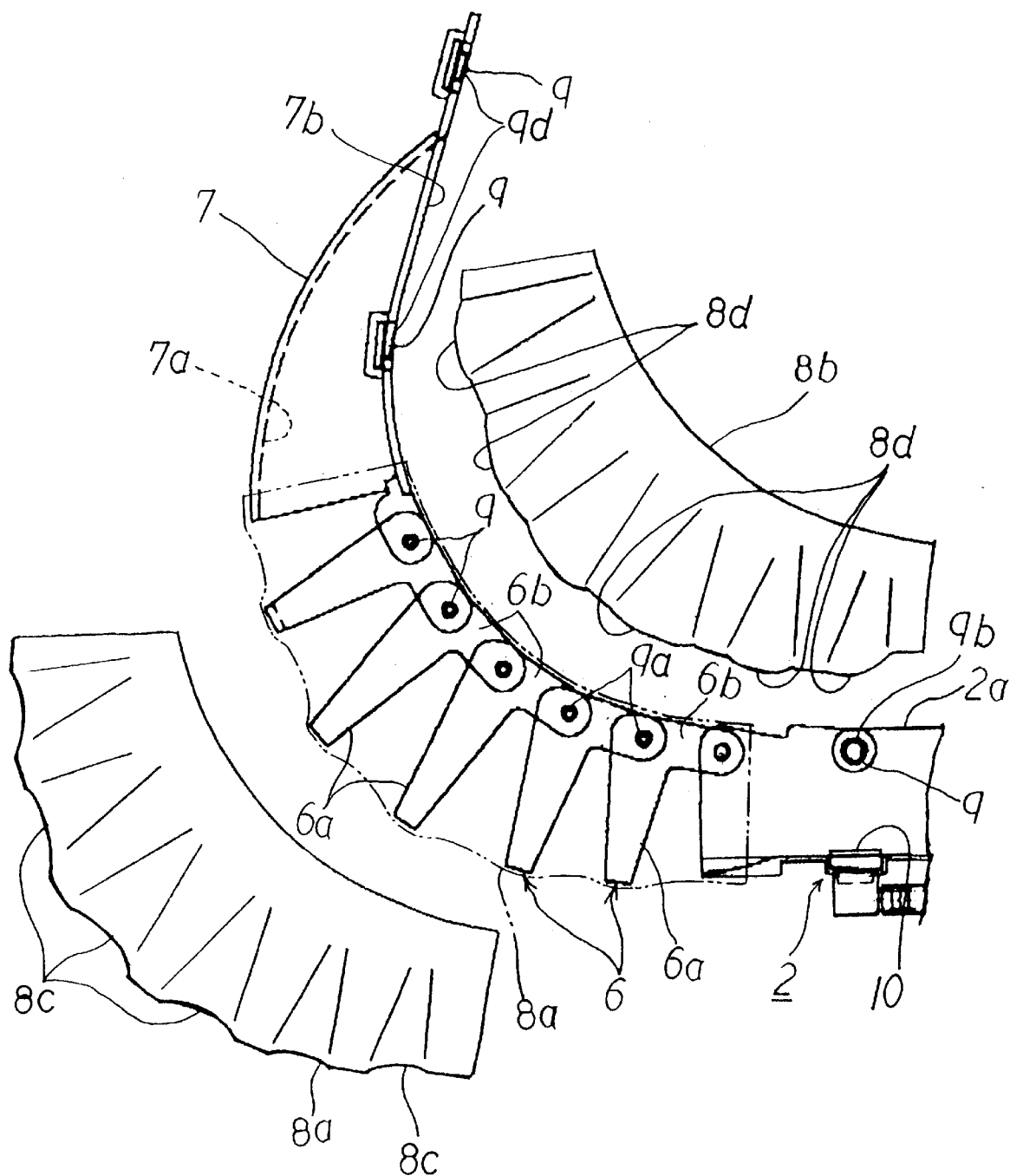
FIG. 5 is a magnified exploded perspective view of concertina joints and waterproof cloth used in the invention.

The concertina joints 6 have inner and outer sides which are respectively covered with waterproof cloths 8a, 8b, as shown in FIG. 5. The cloths 8a, 8b prevent wash water from leaking without interfering with the bending performance of the concertina joints 6. The concertina joints 6 are formed continuous with a cavity 2c, hereinafter described, of the diaper cup main body 2. The concertina joints 6 each comprise a skeleton portion 6a generally in a U-form in section, a connecting portion 6b pivotally supporting each concertina joint 6 for free bending, and pivot holes opened to insert hooks 9a in front and back ends of the connecting portion 6b.

The concertina joints 6 are connected in a continuous manner at each connecting portion 6b by hooks 9 supporting the changeable diaper 3 in the pivot holes. As a result, the concertina joints 6 are allowed to bend and deform, as shown by virtual lines in FIG. 2. The device can thus be fitted on pelvic regions of different sizes to accommodate sick and bedridden persons or the like of various sizes. Also, the front cover 7 forms a curved recess surface 7a continuing a curved surface of the skeleton portion 6a of the concertina joint 6, as shown in FIGS. 1, 2 and 5. The front cover 7 is formed with flanges 7b continuous with the connecting portion 6b of the concertina joint 6, so that the hooks 9d are provided on the flanges 7b.

The waterproof cloths 8a, 8b may be respectively bonded to the whole front and back surfaces, or bonded on front and back surfaces of each of the concertina joints 6. Where the waterproof cloths 8a, 8b are bonded on each concertina joint 6, six waterproof cloths 8a, 8b, for example, are provided continuous on the respective front and back surfaces of the six concertina joints 6 with overlapping bonding points. This allows the waterproof cloths 8a, 8b to be bonded in a bendable and deformable state on the front surface of the concertina joints 6, which is generally spherical in form.

The waterproof cloths 8a, 8b may be formed in one sheet, as shown in FIG. 5. In this case, because the waterproof cloths 8a, 8b are to be bonded on the front and back rounded surfaces of the bend-deformable concertina joints 6, it has spherical areas 8c, 8d formed by pressing a flat strip cloth generally into a spherical form. The waterproof cloths 8a, 8b are also preferably coated with a water preventive agent. The waterproof cloths 8a, 8b are bonded on the concertina portions and skeleton portions 6a of the concertina joints 6 through an adhesive. The waterproof cloths 8a, 8b, if formed in one sheet, can reduce the number of processes of bonding and dry time of the adhesive.

Figure 6:
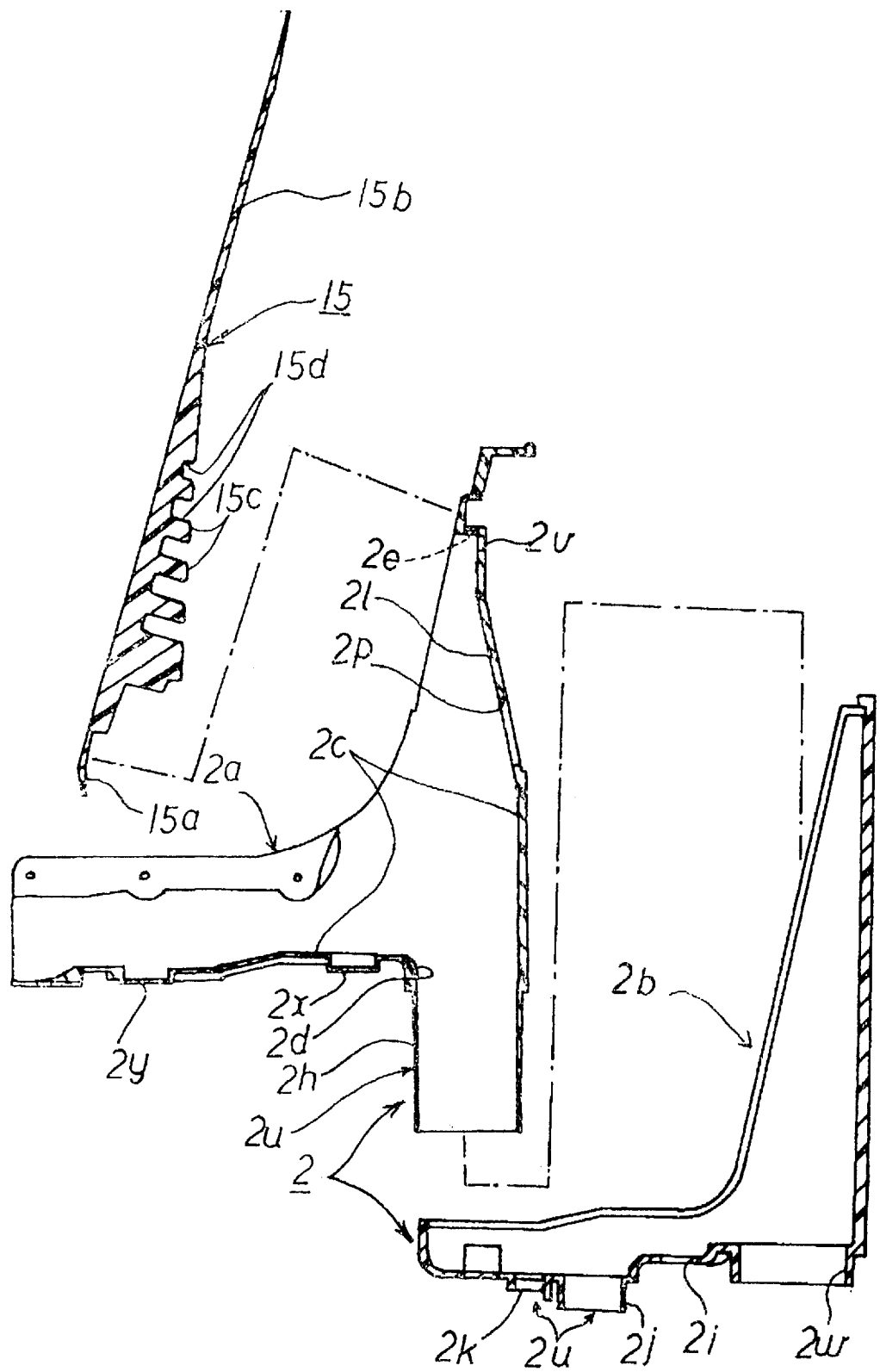
FIG. 6 is an explanatory view of an upper cup, a lower cup and a waist-fit sheet used in the invention.

The diaper cup main body 2, as shown in FIG. 6, is bonded together into one body with an upper cup 2a provided on a side to contact a human body, and a lower cup 2b positioned on an outer side when attached to the human body. The diaper cup main body thus forms a space A at an interior, as shown in FIG. 2. The diaper cup main body 2 is connected into a generally U-form with a front cover 7 to cover a front side of the pelvic region. The diaper cup main body 2 is formed of a hard urethane resin. The concertina joints 6 and a waist-fit seat 15 to cover a back side of the pelvic region are formed of semi-hard urethane resin for covering the entire pelvic region.

The diaper cup main body 2 has hooks 9b, 9c, a private-parts wash nozzle 10, an anus wash nozzle 11, a cup wash nozzle 12, a feces-detecting sensor 13, and a urine-detecting sensor 14, as shown in FIGS. 1 and 2.

The diaper cup main body 2 is connected to an external equipment through use of an excrement-suction hose 16, a wash-water feed hose 17, an air feed hose 18, and a sensor coupler 2k. The excrement-suction hose 16 is used to suck the wash water and excrement in an inside of the diaper cup unit 1. The wash-water feed hose 17 is used to feed wash water to the inside of the diaper cup main body 2. The air feed hose 18 is used to feed warm air to the inside of the diaper cup main body 2. And, the sensor coupler 2k is used to derive electric signals from the feces-detecting sensor 13 and urine-detecting sensor 14.

The upper cup 2a is formed of a hard urethane resin or the like generally in a J-form, as viewed in cross section. The upper cup 2a is arranged, as shown in FIG. 6, with a discharge port 2d provided at a center on a surface side, a connection cylinder portion 2h continuous to the discharge port 2d and connecting to the excrement-suction hose 16, cavities 2c provided on respective sides of the discharge port 2d, nozzle setup holes 2v formed in the cavities 2c to install cup-wash nozzles 12, a nozzle setup hole 2x to install an anus-wash nozzle 11, a nozzle setup hole 2y to install a private-parts wash nozzle 10, a plurality of the hooks 9b in inner upper ends of side walls on left and right sides of the cavity 2c, hooks 9c in left and right edges 2t of the cavity 2c, and air-blow ports 2e, 2f, 2g on a side of the waist-fit seat 15.

The upper cup 2a is formed, in a joining surface on the backside to the lower cup 2b, with inner walls 2m forming the space A to pass air from the connecting cylinder portion 2j to the air blow ports 2e, 2f, 2g through the air feed hose 18. The air entered in the space A through the connecting cylinder portion 2j is branched to the left and right of the connecting cylinder portion 2h connecting to the excrement suction hoses 16, as shown at arrows a and b of FIG. 7. The air entered in the space A is further guided by the inner wall 2m, thus flowing toward the air blow ports 2e, 2f, 2g, as shown at arrows c and d.

Figure 7:
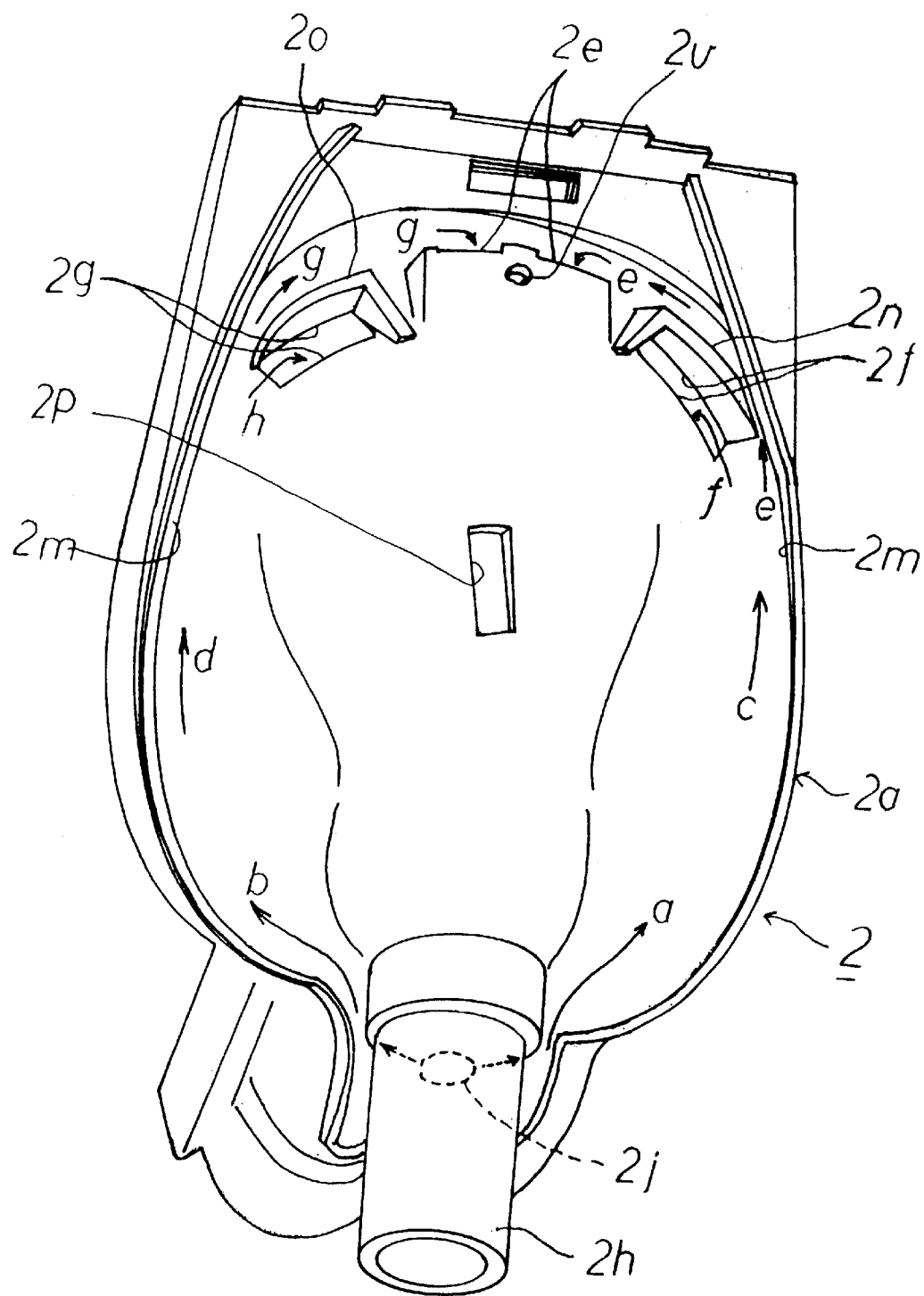
FIG. 7 is a magnified perspective view of the upper cup of the invention.

The air at the arrows c and d, at both left and right, is separated into arrows e and f and arrows g and h, respectively, by a guide wall 2n, 2o generally in an L-form. The air at the arrows e and g flows along the inner wall 2m and passes from the space A to the hot air blow port 2e and then out to a surface of the upper cup 2a. Meanwhile, the air at the arrows f and h is guided on the guide walls 2n and 2o and passes the air blow ports 2f and 2g and then goes out to a surface of the upper cup 2a. A penetration hole 2p, as shown in FIG. 7, is provided for installing a feces-detecting sensor 13.

The guide walls 2n and 2o are walls formed generally in an L-form on center and outer-edge sides of the air blow ports 2f, 2g on the left and right to thereby flow air in equivalent amounts and with good balance through the three air blow ports 2e, 2f, 2g. The guide walls 2n, 2o collect air to the left and right air blow ports 2f, 2g, thereby increasing the amount and intensity of air flow through the left and right air blow ports 2f and 2g.

On a surface side of the air blow ports 2e, 2f, 2g, flaps 21 are fixed through screws 22, as shown in FIGS. 3, 4, 8 and 9. The flaps 21 are guides to increase the intensity of air flow to the surface of the upper cup 2a through the air blow ports 2e, 2f, 2g to reduce air turbulence. The flaps 21 also direct the flow of air from a bottom of the cavity 2c to the discharge port 2d, thereby causing excrement and wash water to flow toward the discharge port 2d with smoothness and efficiency.

Figure 8:
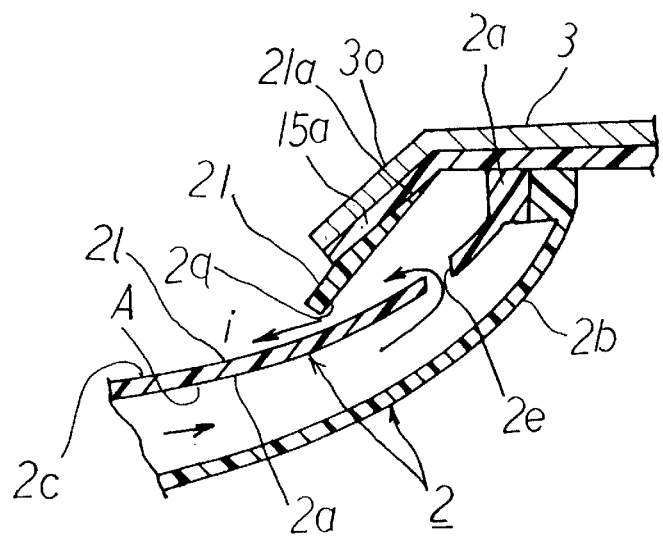
FIG. 8 is a sectional view showing an apron of a changeable diaper of the invention.
Figure 9:
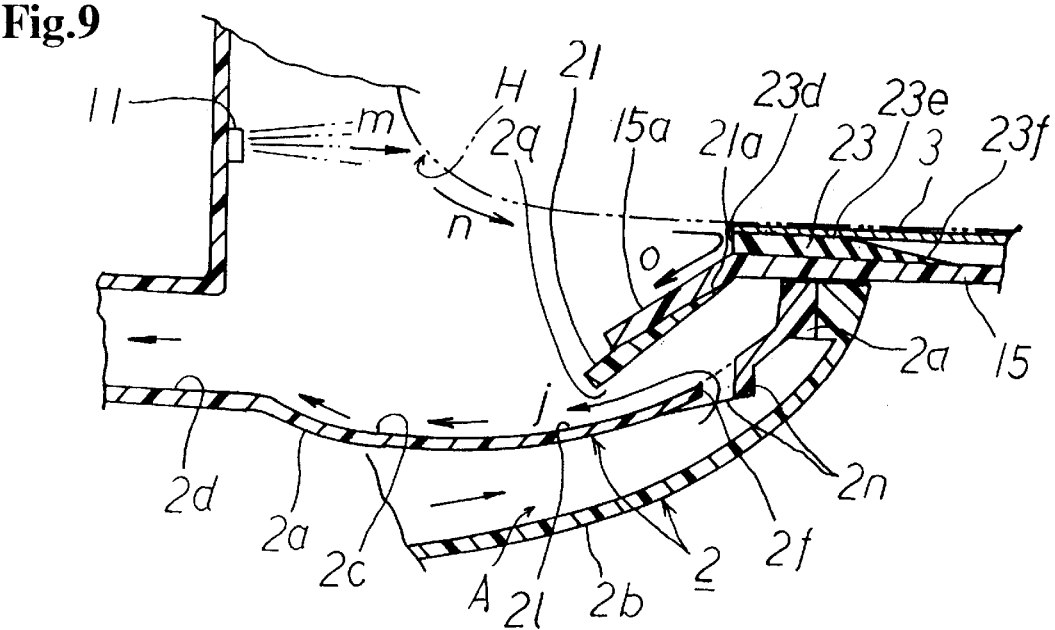
FIG. 9 is a sectional view showing a setup state of a waterproof dam of the invention.

The flap 21 is generally in an arcuate form long in a sideways direction and formed of a semi-hard urethane resin sheet. The flap 21 has a wedge-formed portion 21a on a side of the waist-fit seat 15, as shown in FIGS. 8 and 9. The flaps 21 cover the air blow ports 2e, 2f, 2g, as shown in FIGS. 8 and 9, and are arranged at an upper end in a slant surface 21 of the diaper cup main body 2.

Figure 10:
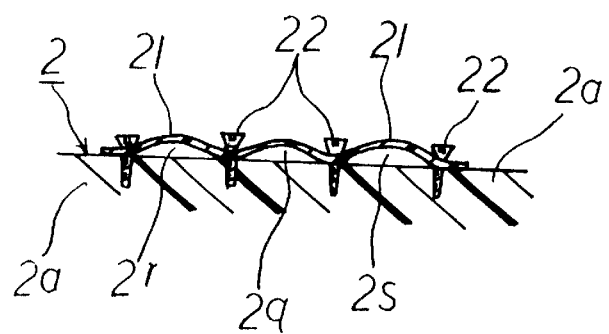
FIG. 10 is a sectional view showing a shape of an outlet port of the invention.

The flap 21 is formed with the wedge-formed portion 21a at one end and the other end directed to the slant surface 21 of the diaper cup main body 2. The flap 21 thereby provides an air blow port 2q, 2r, 2s as a thickness-reduced port. Also, the flaps 21 can make long the shape and decrease the aperture size of the outlet port 2q, 2r, 2s by fixing the side portions of the three air blow ports 3e, 3f, 3g with four screws 22 on a diaper cup main body 2, for example, as shown in FIG. 10. This makes it possible to flow air immediately along a bottom of the entire slant surface 21 and the cavities 2c of the diaper cup main body 2, as indicated by arrows i and j in FIGS. 8 and 9.

Figure 3:
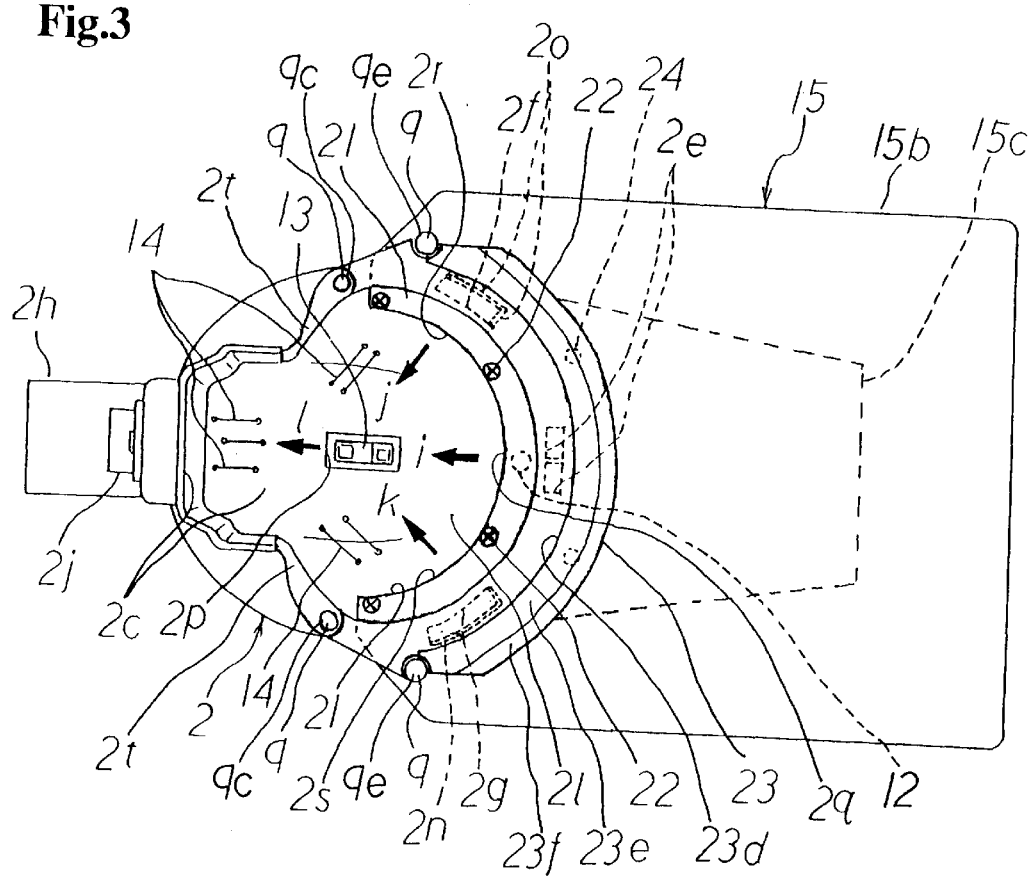
FIG. 3 is a front view of the diaper cup main body of the invention.
Figure 4:
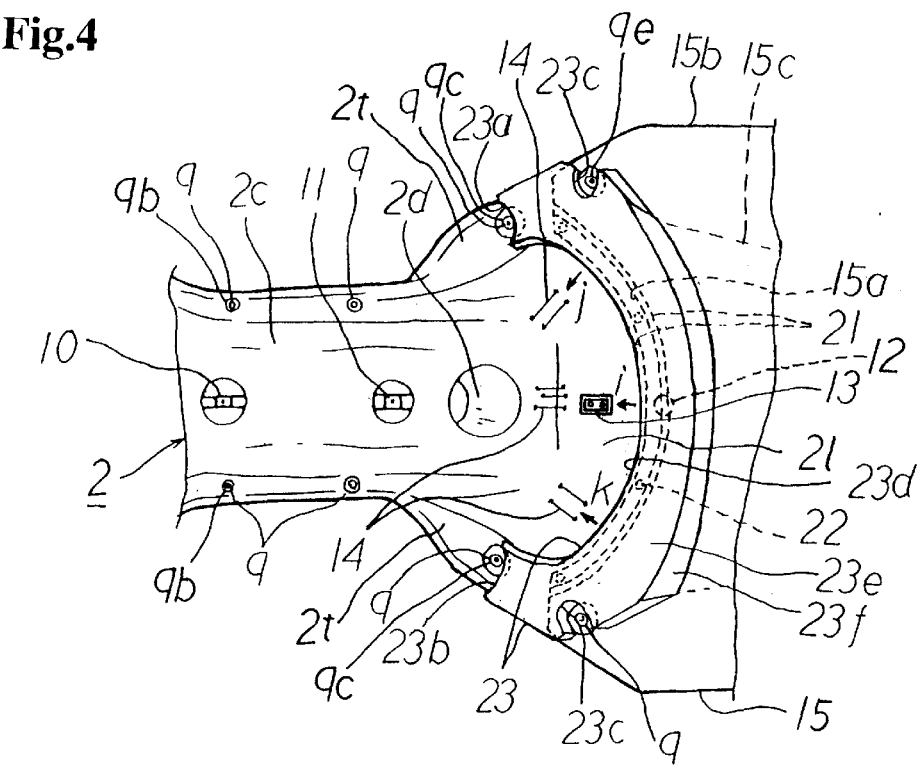
FIG. 4 is a plan view of the diaper cup main body of the invention.

The air blown out of the outlet port 2q, 2r, 2s flows toward the discharge port 2d, as shown at arrows i, j, k, l, because the flap 21 has an arcuate form, as shown in FIGS. 3 and 4. As a result, when a sick person is in a lying state, wash water and urine are splashed smoothly toward the discharge port 2d side, preventing the same from staying in the diaper cup main body 2, and also preventing erroneous operation to discharge urine. Also, feces can be floated and washed, without remainder, out of the cavity 2c of the diaper cup main body 2 by the air from the outlet ports 2q, 2r, 2s and wash water through the anus wash nozzle 11 and cup wash nozzle 12.

Incidentally, the screws 22 in the diaper cup main body 2 are screws made in a same color as the diaper cup main body 2 (e.g., with white paint) so as not to provide a sick person with a feeling of metal mechanical coolness.

A support portion 15a generally in an arcuate form is provided on the flap 21. The support portion 15a is formed at an end of the waist-fit seat 15 to prevent the flap 21 from spreading due to the force of airflow and to provide reinforcement.

Figure 11:
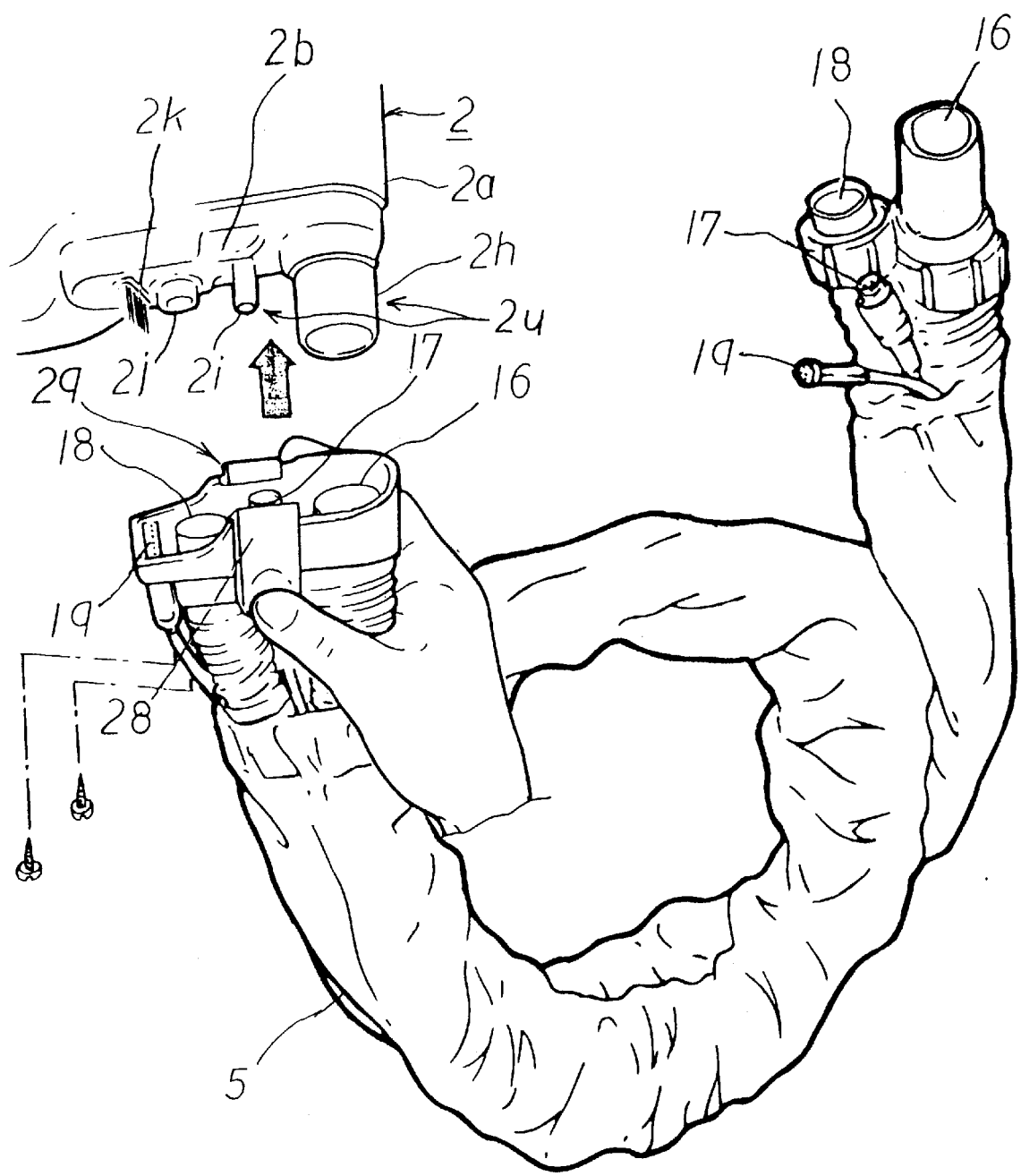
FIG. 11 is a waist-region exploded perspective view showing a structure of a hose connection portion of the diaper main body of the invention.
Figure 12:
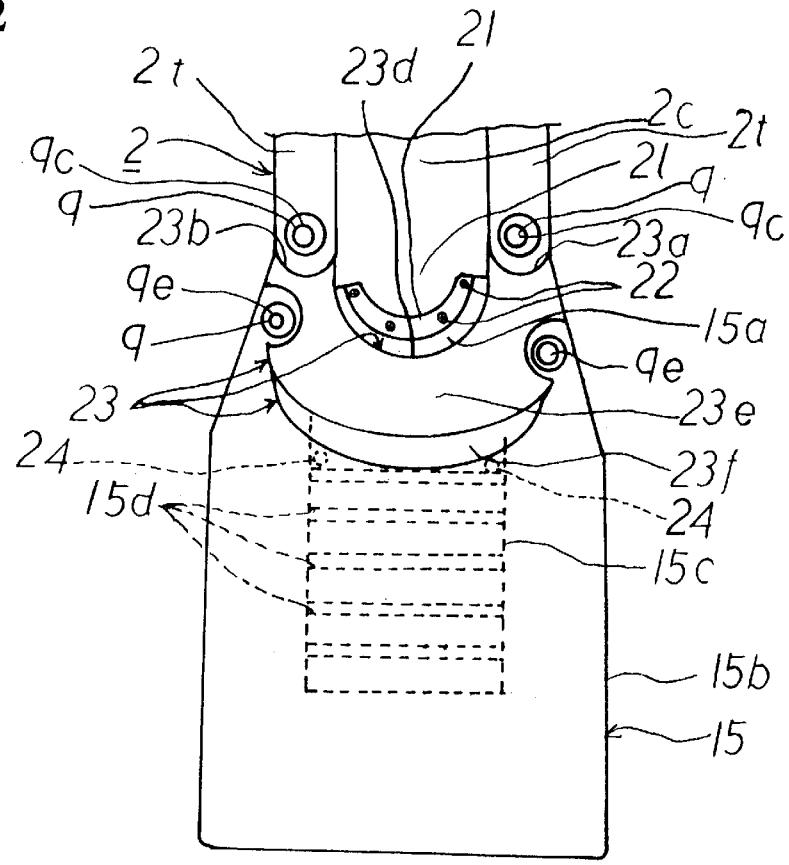
FIG. 12 is a plan view showing a setup state of a waterproof dam of the invention.
Figure 13:
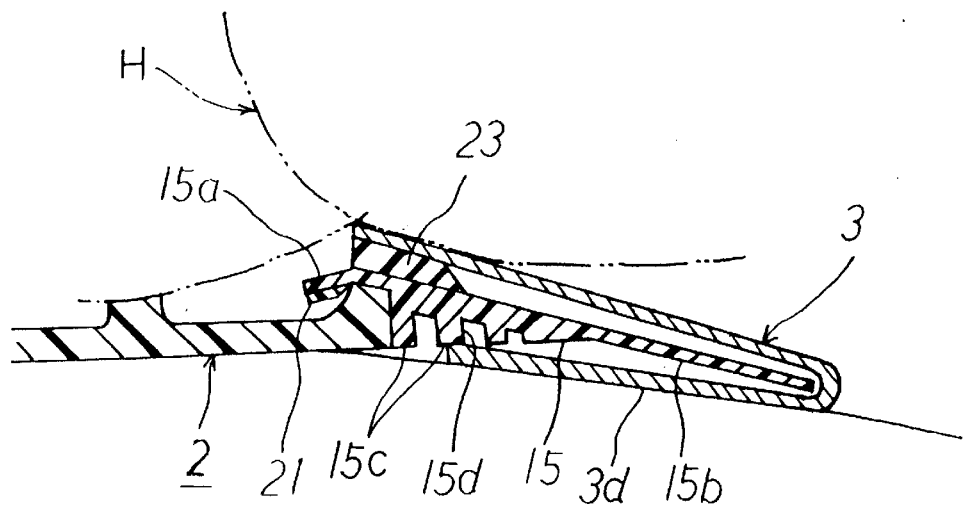
FIG. 13 is a sectional view showing a setup state of a waterproof dam of the invention.

The lower cup 2b of the diaper cup main body 2 is formed of a hard urethane resin similar to the upper cup 2a. As explained above, the lower cup 2b, if joined with an underside of the upper cup 2a, forms a space A with the upper cup 2a. The upper cup 2a and lower cup 2b together form the diaper main body 2. The lower cup 2b is formed, as shown in FIGS. 2, 6 and 11, with a hose connecting portion 2u integrally forming a penetration hole 2w in which the connecting cylinder portion 2h of the upper cup 2a is to be fitted. The lower cup 2b also has a connecting portion 2i to connect between a wash-water feed hose 17 and a water feed pipe 20, a connecting cylinder portion 2j to connect an air-feed hose 18 to feed air into the space A, and a sensor coupler 2k to connect to a cord 19 connected to a power supply or the like.

The excrement suction hose 16 is connected to a vacuum motor or vacuum pump (not shown) by way of an excrement tank (not shown) and vacuum hose (not shown). The wash-water feed hose 17 is connected to a wash-water ejection adjust valve (not shown). The air feed hose 18 is connected to the vacuum motor or vacuum pump. The sensor coupler 2k is connected to a sequencer (not shown) through a sensor signal line (not shown).

Incidentally, the vacuum motor or vacuum pump is accommodated, together with a filter box, air discharge pipe and motor-cooling air suction pipe, in a housing. Also, the excrement suction hose 16 and the wash-water feed hose 17 are coupled together by a drain valve, and the warm water tank is connected with a water discharge valve.

As shown in FIG. 2, the space A provides a space to lay a water feed pipe 20 connected to the private-parts wash nozzle 10, the anus wash nozzle 11, and the cup wash nozzle 12. The space A also provides a space to lay a cord 19 connected to a feces-detecting sensor 13 and urine-detecting sensor 14, and functions as a feed air pipe to feed the air from the air feed hose 18 to the air blow ports 2e, 2f, 2g.

The cavity 2c is a semispherical recess formed in the upper cup 2a, which is formed continuous with a slant surface 21 on the side of the waist-fit seat 15, as shown in FIG. 2. The cavity 2c is arranged, in its bottom surface, with the private-parts wash nozzle 10, the anus wash nozzle 11, the feces-detecting sensor 13, and the urine-detecting sensor 14. Also, around the cavity 2c and in the front cover 7 are provided in line a plurality of hooks 9 comprising hooks 9a, 9b, 9c, 9d, 9e to attach and detach the changeable diaper 3.

The private-parts wash nozzle 10 and the anus wash nozzle 11 are nozzles used exclusively for individually washing the private parts and anus, respectively, of a sick person wearing the diaper cup unit 1, as shown in FIG. 2. The ejection range θ1 of the private-parts wash nozzle 10 is set wide as compared to the ejection range θ2 of the anus wash nozzle 11.

The cup wash nozzle 12 is a nozzle to wash away the excrement excreted by a sick person, as shown in FIG. 2, which is arranged on an inner side of the flaps 21 in the vicinity of the air blow port 2e for blowing warm air. The cup wash nozzle 12 operates to eject wash water toward the side of the feces-detecting sensor 13. The cup wash nozzle 12 is fitted in a nozzle setup hole 2v opened in a center nearby the right and left air blow ports 2e, as shown in FIG. 7.

The feces-detecting sensor 13 is a sensor to detect the feces excreted by a sick person or the like. The feces-detecting sensor 13 comprises, for example, one sensor installed at a center location in the slant surface 21, as shown in FIGS. 2 to 4.

The urine-detecting sensor 14 is a sensor to detect the urine excreted by a sick person or the like. As shown in FIGS. 1 to 4, sensors comprising, for example, two to three conductor wires are installed, for example, at three locations. A first location for the sensors is from the air blow ports 2e, 2f, 2g to a center of the cavity 2c in the vicinity of the lower discharge port 2d. Other locations for the sensors are on the side walls at the left and right sides of the lower discharge port 2d and directed toward the discharge port 2d.

The waist-fit seat 15 is a plate on which a sick person or the like rests his or her waist. The seat 15 is formed of semi-hard urethane resin having a hardness, for example, of approximately 70 [Hs]. The waist-fit seat 15 is formed integral with a flat, bendable or deformable plate portion 15b, a support portion 15a formed on a side of the plate portion 15b facing the cavity 2c, and a slant portion 15c installed in an outward center.

The waist-fit seat 15 has an inner surface which is slanted in its entirety due to the slant portion 15c provided in the outer center. The slant portion 15c is formed with a plurality of cutout grooves 15d which extend laterally and provide a structure that is easy to bend or deform. The waist-fit seat 15 is easy to deform due to the cutout grooves 15d so that a sick person or the like wearing the diaper main body 2 can easily and freely change his or her position. Thus, the sick person or the like can rise from the bed easily. The waist-fit seat 15 is fixed to the diaper main body 2 through adhesive and further firmly fixed by screws 24.

A waterproof dam 23 having a generally arcuate form is arranged around the support portion 15a of the waist-fit seat 15 where a coccyx is positioned when the diaper cup main body 2 is worn by a sick person or the like. The waterproof dam 23 comprises a buffer member, for example, of silicone rubber having a hardness of approximately 7 [Hs]. The waterproof dam 23 provides a buffer member in a position that a coccyx of a sick person abuts against, and also prevents wash water or urine from leaking outside the diaper cup main body 2.

In the waterproof dam 23, when the wash water ejected in a direction of arrow m through the anus wash nozzle 11 hits a pelvic region H of a sick person or the like, as shown in FIG. 9, the water with the impetus flows in a direction of arrow n along a surface of the pelvic region H to hit against the waterproof dam 23. The wash water hitting the waterproof dam 23 then hits an end of the waterproof dam 23 and is repelled back in a direction of arrow o to flow through the slant surface 21 of the diaper cup main body 2. Then, the wash water flows together with the air flow in the direction of arrows i, j and k from the exit ports 2q, 2r and 2s and toward the discharge port 2d.

The waterproof dam 23 comprises, as shown in FIG. 4, opposite ends 23a, 23b rested on opposite bank-like edges 2t on both sides of the cavity 2c and matched to a half periphery of the hook 9c. The waterproof dam 23 also has a hook buffer portion 23c covering a half periphery of another hook 9e, an arcuate dam portion 23d that meets an outer edge of the slant surface 21 of the diaper cup main body 2, a flat surface portion 23e that receives the load of a sick person or the like, and a slant portion 23f formed continuous with the flat surface portion 23e. The waterproof dam 23 is fixed through adhesive on the diaper cup main body 2 and the waist-fit seat 15.

The ends 23a, 23b of the waterproof dam 23 provided at both edges 2t of the diaper cup main body 2 provide a waterproof effect of eliminating a gap between a pelvic region H of a sick person or the like and the diaper cup main body 2, thereby preventing wash water or urine from leaking. Also, the ends 23a, 23b and buffer portion 23c prevent the hooks 9c, 9e provided on the diaper cup main body 2 and the waist-fit seat 15 from abutting against a sick person or the like, thereby preventing irritation of the skin of the sick person or the like.

The dam portion 23d reflects wash water or urine. The dam portion 23d comprises a soft material and provides a close contact between the waist-fit seat 15 and the changeable diaper 3, thereby preventing the water content from intruding through between the waist-fit seat 15 and the changeable diaper 3. This prevents against wetting in the diaper cover 4 or bed sheet. When receiving a body weight of a sick person or the like, the flat surface portion 23e and slant portion 23f will not irritate the skin of the sick person or the like, because the waterproof dam 23 is formed of a soft material.

The changeable diaper 3 of the invention will now be described. The changeable diaper 3 has, as shown in FIG. 1, an elongate hole 3e opened in a center to insert the hose connecting portion 2u, a side-leak preventive frill 3a provided on left and right sides of the elongate hole 3e, a magic tape 3c (for example, a fastening tape available under the trademark VELCRO) to be joined with a corresponding magic tape 4a of the diaper cover 4, a bag 3d into which the waist-fit seat 15 is to be inserted, a waist cover 3k for resting on the waist of a sick person or the like, and a bag 31 into which the buffer member 25 is to be inserted.

The changeable diaper 3 is attached by engaging between the hook 9 having the hooks 9a, 9b, 9c, 9d, 9e on the inner side of the diaper cup main body 2 and the hook 3b provided around the elongate hole 3e, thereby being wound around the pelvic region H of a sick person or the like. The changeable diaper 3 is provided around the cavity 2c of the diaper cup main body 2, and comprises a wrap portion 3f provided around the cavity 2c of the diaper cup main body 2 to cover the pelvic region H of a sick person or the like, and tightening strip portions 3g, 3h for turning the waist of the sick person or the like. The changeable diaper 3 is formed, for example, of a nylon cloth material generally in a T form in its entirety.

Figure 14:
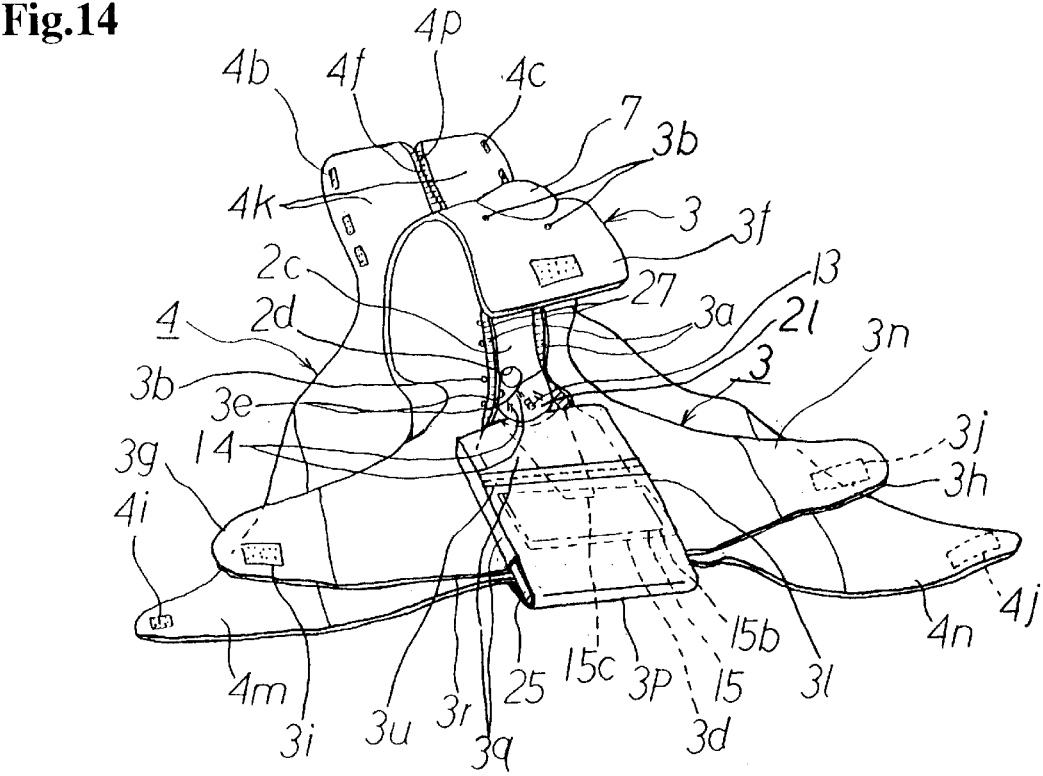
FIG. 14 is a perspective view showing an assembling state of the invention.

The side-leak preventive frills 3a are provided on both sides of the elongate hole 3e on the inner side of the changeable diaper 3 in a manner covering a head of the hook 3b, as shown in FIGS. 1 and 14. The side-leak preventive frill 3a is formed, for example, of a waterproof-treated nylon cloth and sewed with corrugation for expansion and contraction. The left and right side-leak preventive frills 3a have, at their ends, respective waterproof cloths 27 internally provided with a rubber string 26, as shown in FIG. 18.

Figure 18:
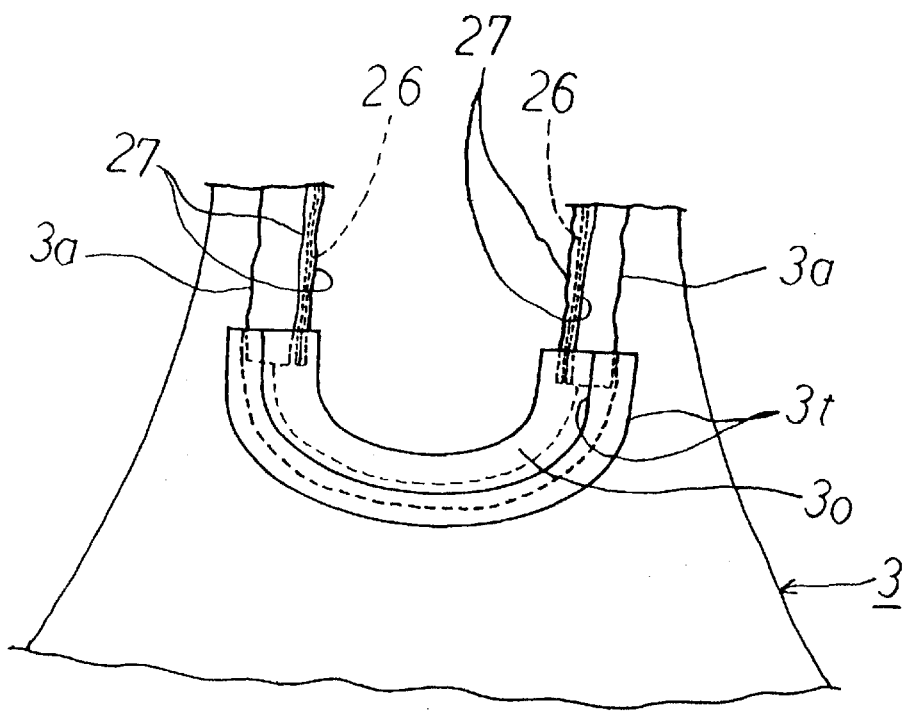
FIG. 18 is a plan view showing a setup state of the apron of the invention.
Figure 19:
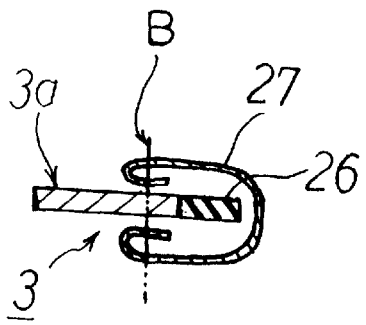
FIG. 19 is a sectional view showing a setup state of a rubber string of the invention.

The rubber string 26 is sewed in an end of the side-leak preventive frill 3a, as shown in FIGS. 18 and 19. The rubber string 26 is covered by waterproof cloth 27, and sewed to the side-leak preventive frill 3a by a waterproof thread B with the waterproof cloth 27 bent at its both ends. This prevents against wetting in an outer side of the changeable diaper 3 or diaper cover 4 due to the rubber string 26 having a nature of absorbing and conveying water content.

The hook 3b is firmly fixed, for example, in a hole opened around the elongate hole 3e in the changeable diaper 3, by press-fitting the members on the front and back sides. The hook 3b is provided in a hidden state at the rear of the side-leak preventive frill 3a on the inner side of the changeable diaper 3, as shown in FIGS. 1 and 14. The hook 3b fits with the hooks 9b, 9c, 9e provided around the cavity 2c of the diaper cup main body 2, the hook 9a provided at the edge of the concertina joints 6 continuing to the cavity 2c, and the hook 9d provided at the flange 7b of the front cover 7 continuing to the concertina joints 6, thereby fixing the changeable diaper 3. The magic tapes 3c, 3i, 3j can be adjusted in length to accommodate differences in the size of a pelvic region H of a person to wear the changeable diaper 3.

The tightening strip portions 3g, 3h are attached with magic tapes 3i, 3j in the respective left and right corresponding positions, as shown in FIGS. 1 and 14. The strip portions 3g and 3h thus serve as a belt to wear the diaper cup main body 2 on a pelvic region H of a sick person or the like. The changeable diaper 3 also comprises a surface cloth 3m, a lining cloth 3n, and an absorbent mesh cloth (not shown) interposed between the surface cloth 3m and the lining cloth 3n. The mesh cloth comprises a nylon cloth improved in absorbability, for example, by increasing the in-cloth space. The surface cloth 3m and the lining cloth 3n are sewed with dense cloth fiber, as compared to the mesh cloth.

Figure 16:
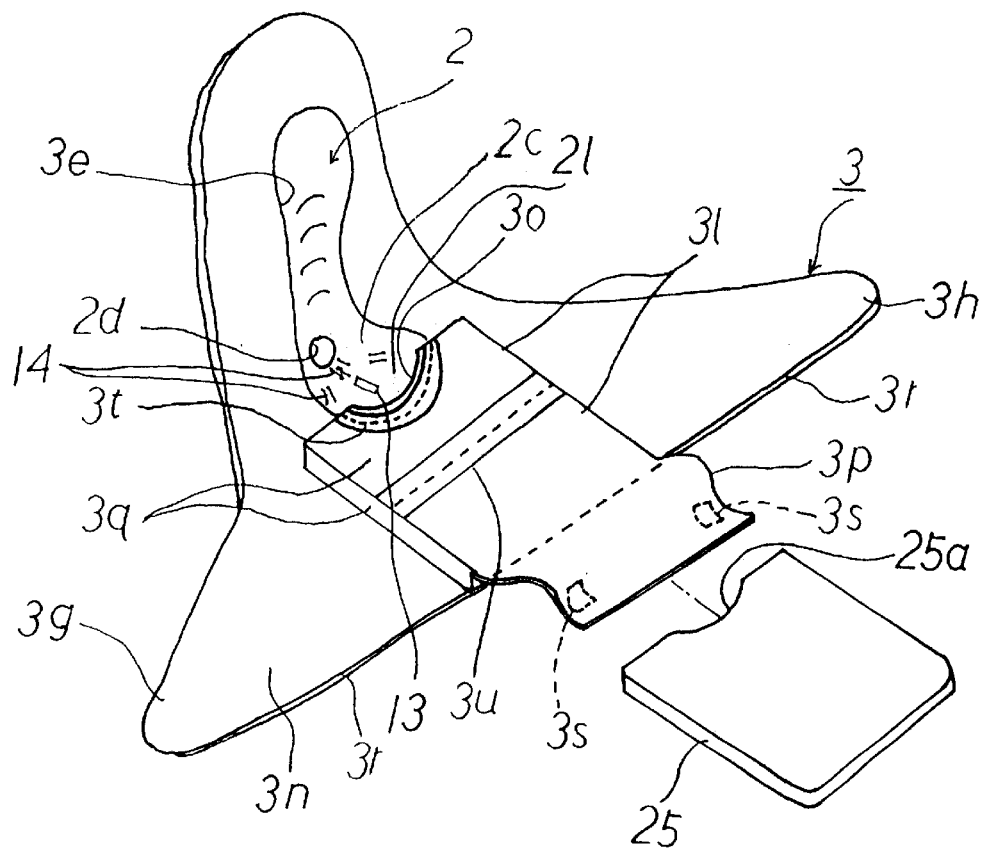
FIG. 16 is a perspective view showing a state when assembling the buffer member to the changeable diaper of the invention.
Figure 17:
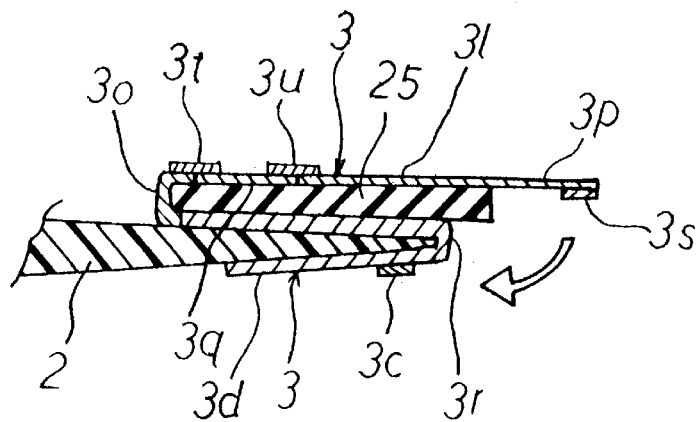
FIG. 17 is a sectional view showing a setup state of the buffer member of the invention.

Incidentally, in the changeable diaper 3, where a waterproof dam 23 is not provided in the diaper cup unit 1, an apron 3o is provided formed of a waterproof cloth in an edge on a bag 31 side of the elongate hole 3e. The apron 3o extends from the support portion 15a of the waist-fit seat 15 into the diaper cup main body 2, as shown in FIGS. 8, 16 and 18. This prevents wash water or urine from leaking through between the waist-fit seat 15 in a peripheral position of the apron 3o and the changeable diaper 3.

Figure 20:
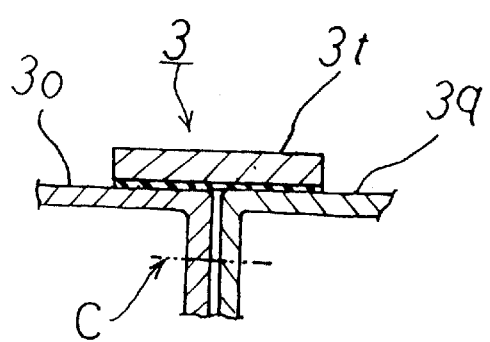
FIG. 20 is a sectional view showing a setup state of a waterproof sheet of the invention.

As shown in FIGS. 16, 18 and 20, water preventive sheets 3t, 3u are bonded on a seam C between the apron 3o and the bag 31 and a seam between the waterproof cloth 3q and the bag 31. This prevents water from leaking through the seam of the apron 3o and the bag 31 or a seam of the waterproof cloth 3q and the bag 31.

Figure 15:
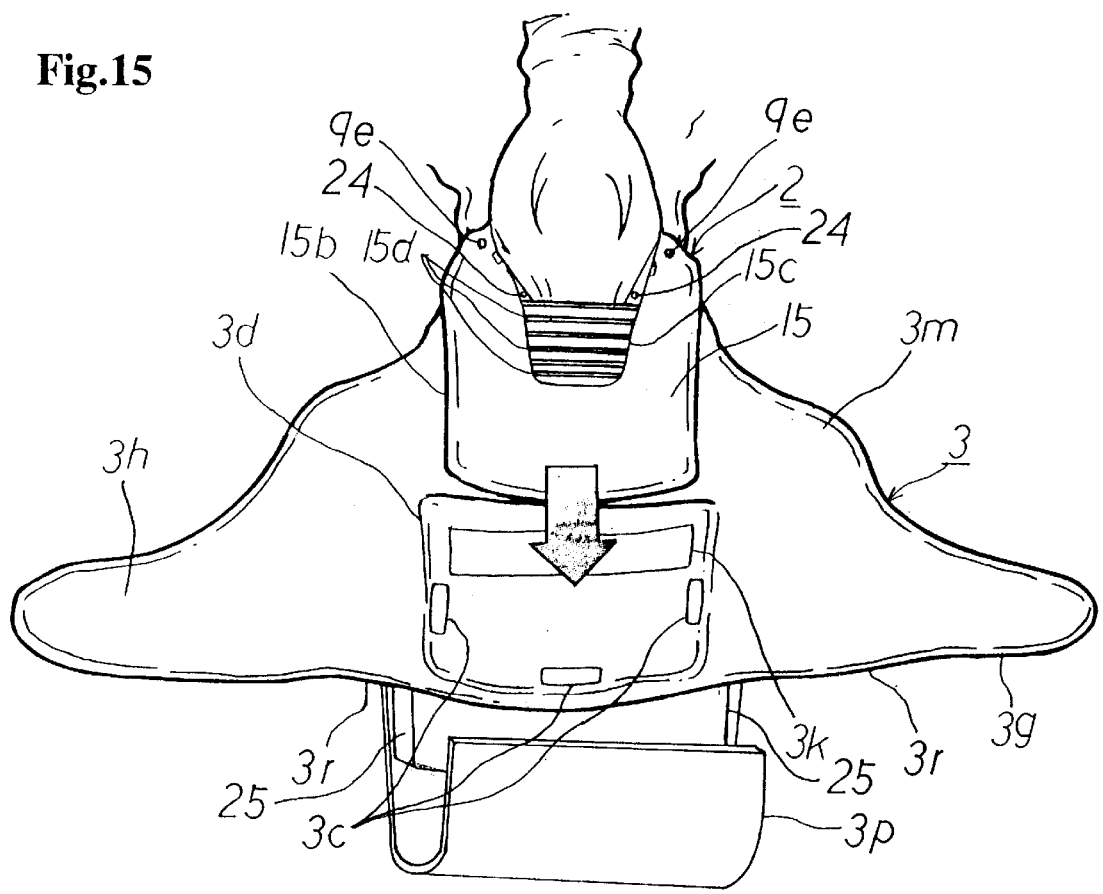
FIG. 15 is a front view showing a state when assembling the waist-fit seat to the changeable diaper of the invention.

The changeable diaper 3 has a bag 3d on its backside into which the plate-like portion 15b of the waist-fit seat 15 is inserted, as shown in FIG. 15. By inserting the plate-like portion 15b of the seat, the changeable diaper 3 is prevented against rumples due to the rigidity of the plate-like portion 15b. Thus, the skin of a sick person or the like will be contacted with a stretched state of the changeable diaper 3 without rumples, thereby preventing irritation of the sick person's skin. The bag 31 for inserting the buffer member 25 is formed on a surface side of the changeable diaper 3 to be contacted with a pelvic region H, as shown in FIGS. 1, 14, 16 and 17.

The bag 31 has a close cover 3p for covering an insertion port for inserting the buffer member 25. The buffer member 25 can be fixed in the bag 31 by covering the close cover 3p and joining the magic tape 3s to the magic tape 3c on the surface side, as shown in FIG. 16. The side surface and the elongate side 3e of the bag 31 comprises a waterproof cloth 3q.

The buffer member 25 comprises a gel sheet that can receive dispersedly a body weight of a sick person or the like. This prevents bedsores of the sick person or the like. The buffer member 25 comprises, for example, a soft, thick plate (available, for example, under the trademark ACTIONPAD). The plate for the buffer member 25 is selected so that it will not have a reaction force upon undergoing a weight, which is free from adhesion at its bottom, and has a pressure-dispersion effect. The plate is soft and ready to deform upon undergoing load, but has an excellent restoration force. The plate also helps to prevent sultry feeling caused by the device, and does not irritate the skin.

The buffer member 25 and bag 31 at one end close to the cavity 2c are formed with a cutout portion 25a in an arcuate form matched to the shape of the dam portion 23d of the waterproof dam 23, as shown in FIG. 16. The other end of the buffer member 25 is formed long to extend from the upper end 3r, as shown in FIGS. 1, 14 and 16. This shape prevents the upper end 3r of the changeable diaper 3 from pressing against a sick person, or the like and irritating the skin.

The diaper cover 4 of the invention will now be described. As shown in FIGS. 1 and 14, the diaper cover 4 has magic tapes 4a, 4b, 4c, 4d, 4e, 4i, 4j, a fastener 4f, a hose-unit pass hole 4g, and a hose-unit enclosure portion (not shown).

The diaper cover 4 is generally in a T-form similar to the changeable diaper 3.

The diaper cover 4 is a cloth member comprising a pelvic-region enclosure portion 4k to cover the enclosure portion 3f, and wrap portions 4m, 4n that correspond generally to the tightening strip portion 3g, 3h. The diaper cover 4 has a cut portion 4p extending from the hose-unit enclosure portion to the hose-unit pass hole 4g. The cut portion 4p separates the diaper cover 4 to its outer side. The fastener 4f is arranged in the cut portion 4p to close the cut portion 4p when the device is assembled.

The diaper cover 4 and the changeable diaper 3 are attached together by joining the magic tape 4a on the diaper cover 4 to the magic tape 3c on the changeable diaper 3.

The diaper cover 4 itself is fixed on a human body by joining the magic tapes 4a, 4b, 4c, 4e, 4i, 4j to the diaper cover 4, which is preferably made of a French-pile cloth. The fastener 4f is provided so that the fastener 4f can be opened to take out only the diaper cover 4 when the diaper cup main body 2 is connected with the hose connecting portion 2u.

The pelvic-region enclosure portion 4k is made for free movement by separating from the hose-unit enclosure portion below the hose-unit pass hole 4g to an upper end and sewing a fastener 4f thereon. The hose-unit pass hole 4g is an elongate hole coincident with the hose connecting portion 2u of the diaper main body 2 and made long along a centerline of the diaper cover 4.

The hose-unit enclosure portion is in a cylindrical form and is provided continuous with the hose-unit pass hole to cover and hide the hose connecting portion 2u.

The hose-unit enclosure portion has a fastener 4f arranged longitudinally in a front center, as shown in FIGS. 1 and 14, so that the cylindrical hose-unit enclosure portion can be opened by opening the fastener 4f.

On an upper rear side of the diaper cover 4, an expansion-and-contraction rubber 4q is internally provided, as shown in FIG. 1, so that the upper end of the diaper cover 4 fits a waist region of a human body. Also, a waist fit strip 4r is arranged as a cushion member in a generally center portion of the diaper cover 4.

With the diaper cup main body 2, changeable diaper 3 and diaper cover 4 explained above, the changeable diaper 3 and diaper cup main body 2 are fastened together by the hooks 9a, 9b, 9c, 9d, 9e, 3b. Next, the changeable diaper 3 and the diaper cover 4 are fastened together by the magic tapes 3c, 3i, 3j, 4a, 4b, 4c, 4e, 4i, 4j. Thus, a diaper cup unit 1 is completed as shown in FIG. 14.

In the diaper cup unit 1, the hose unit 29 is connected to the hose connecting portion 2u, as shown in FIG. 11. The hose unit 29 connects the diaper cup unit 1 to external equipment, which has the excrement absorbing hose 16, wash-water feed hose 17, air feed hose 18 and sensor coupler 2k in one body, and collectively supports them. The hose unit 29 is free to attach to and detach from the hose connecting portion 2u positioned in the underside of the diaper cup main body 2. A hold piece 28 is fixed to hardware (not shown) on a side of the diaper cup main body 2. A hose cover 5 is continuous with and overlaps the hose-unit enclosure portion (not shown) of the diaper cover 4.

The present invention having the above structure and operation provides the following effects:

The device for disposing excrement, according to the invention, has a diaper cup main body for enclosing a pelvic region of a human body, a wash-water feed hose connected to the diaper cup main body for feeding wash water into an interior thereof, an excrement suction hose connected to the diaper cup main body for sucking the wash water and excrement in the interior, and an air feed hose connected to the diaper cup main body for feeding air to the inside. The device for disposing excrement is characterized by the diaper cup main body forming a space as a passage to feed air from the air feed hose to an air blow port of the diaper cup main body by joining an upper cup arranged on a side of a pelvic region of a human body and a lower cup matched to the upper cup. Due to this, it is possible to feed air into the diaper cup main body without laying pipes, thereby reducing the number of parts, assembling processes and cost.

Also, the upper cup has a connecting cylinder portion to be connected to the excrement suction hose and the air blow port, and the lower cup has a connecting portion for installing the wash-water feed hose and a connecting cylinder portion to be connected to the air feed hose. Accordingly, connection is possible to the hose unit in a one-touch manner, thus facilitating connection operation.

Also, the diaper cup main body has a water feed pipe and a cord arranged within the space of the diaper cup main body. The water feed pipe is connected to a private-parts wash nozzle and an anus wash nozzle installed in the upper cup. The cord is connected to a feces-detecting sensor and a urine-detecting sensor installed in the upper cup. Accordingly, the cord can be laid within the diaper cup main body in a manner hidden from the outside. Furthermore, the cord is prevented from being loaded with an external force.

Also, the upper cup of the diaper cup main body has a cavity for providing a non-contact state with a human body. The cavity is formed in a surface of the diaper cup main body on a side thereof to be fit on a pelvic region of a human body. The space is formed on a side of the upper cup opposite from the cavity. An inner wall is formed to join the lower cup. The air blow port is formed at a plurality of positions in an upper end of the cavity. This arrangement makes it possible to efficiently splash the excrement deposited in the cavity in a stripping manner and flow it to the discharge port.

Also, the upper cup of the diaper cup main body is preferably formed with an air blow port in an upper end center of the cavity. The air blow port is formed with a guide wall to converge air flowing through the space. This makes it possible to make equivalent the amount of air flow through the air blow ports at the center and left and right and to efficiently blow away the excrement in the side wall side of the cavity of the diaper cup main body.

Also, the diaper cup main body has a flap covering the air blow port on a side to fit on a pelvic of a human body. Accordingly, the air exited through the air blow port can be blown along the bottom surface of the cavity of the diaper cup main body, thereby efficiently blowing away the excrement deposited in the cavity.

Also, the diaper cup main body is formed arcuate in the upper end of the cavity, and the flap is formed generally arcuate and matched to a shape of the upper end of the cavity. The flap is fixed at a plurality of positions, thereby forming an outlet port communicating to the air blow port. This makes it possible to flow air from the center and left and right in the upper end of the cavity of the diaper cup main body, thereby efficiently blowing away the excrement on the left and right side walls in the cavity.

Also, the flap is arranged in a slant surface of the upper end of the cavity of the diaper cup main body and screwed to the diaper cup main body in a side portion of the air blow port. This makes it possible to make the outlet port into a flat, thin form, thereby increasing the strength of airflow through the outlet port and blowing away the excrement.

Also, the diaper cup main body is continuously arranged with a waist-fit seat in the upper end, and the waist-fit seat has a support portion provided overlapping with the flap. Accordingly, the outlet port is spread by the pressure of air, thereby preventing the airflow through the outlet port from decreasing in amount.

Also, the waist-fit seat has a plate-like portion to be inserted in a bag provided in a changeable diaper, and a slant portion provided between the plate-like portion and the support portion and formed with a cutout groove. This makes it possible to make the waist-fit seat easy to bend, and hence, makes it easier for a sick person or the like wearing the diaper cup main body to rise up. Also, due to insertion of the plate-like portion in the changeable diaper bag, it is possible to prevent wrinkles from occurring in a position of the changeable diaper to be laid under a pelvic portion of a human body, and hence, eliminates skin irritation caused by press contact with wrinkles.

Also, the upper cup and the lower cup of the diaper cup main body are formed of a hard resin, and the flap and the waist-fit seat are formed of a resin that is softer than the upper cup and the lower cup and easy to bend and deform. This makes it possible to provide an excrement disposal apparatus that is easy to bend and deform, and hence, easy to fit on a pelvic region of a human body.

Also, the diaper cup main body has a cup-washing nozzle on an inner side of the flap in the vicinity of the air blow port to flow away excrement excreted by a sick person or the like. This makes it possible to arrange the air blow port and cup wash nozzle in the upper end on the back side of the cavity of the diaper cup main body and to feed air and wash water from a corner of the diaper cup main body toward the discharge port, thereby washing away excrement. Also, because the cup wash nozzle is installed in the flap, wash water can be caused to flow through the bottom surface of the cavity of the diaper cup main body in a creeping manner, thereby efficiently washing away deposited excrement in a stripping manner.

What is claimed is:

1. A device for disposing excrement, comprising:
   a diaper cup main body for enclosing a pelvic region of a human body;
   a wash-water feed hose connected to the diaper cup main body for feeding wash water into an interior thereof;
   an excrement suction hose connected to the diaper cup main body for sucking the wash water and excrement from the interior; and an air feed hose connected to the diaper cup main body for feeding air to the interior;

wherein said diaper cup main body forms a space as a passage to feed air from said air feed hose to an air blow port of said diaper cup main body by joining an upper cup arranged on a side to contact a pelvic region of a human body and a lower cup matched to said upper cup; and a water feed pipe and a cord arranged within the space of said diaper cup main body, said water feed pipe being connected to a private-parts wash nozzle and an anus wash nozzle installed in said upper cup, and said cord being connected to a feces-detecting sensor and a urine-detecting sensor installed in said upper cup.

2. A device for disposing excrement as claimed in claim 1, wherein said upper cup has a connecting cylinder portion to be connected to said excrement suction hose and said air blow port, and said lower cup having a connecting portion for installing said wash-water feed hose and a connecting cylinder portion to be connected to said air feed hose.

3. A device for disposing excrement as claimed in claim 1, wherein said upper cup of said diaper cup main body has a cavity formed in a surface of said upper cup on a side thereof to be fit on a pelvic region of a human body, said space being formed on a side of said upper cup opposite from said cavity, and an inner wall formed to join said lower cup, and said air blow port being formed at a plurality of positions in an upper end of said cavity.

4. A device for disposing excrement, comprising:

a diaper cup main body for enclosing a pelvic region of a human body;

a wash-water feed hose connected to the diaper cup main body for feeding wash water into an interior thereof;

an excrement suction hose connected to the diaper cup main body for sucking the wash water and excrement from the interior; and an air feed hose connected to the diaper cup main body for feeding air to the interior;

wherein said diaper cup main body forms a space as a passage to feed air from said air feed hose to an air blow port of said diaper cup main body by joining an upper cup arranged on a side to contact a pelvic region of a human body and a lower cup matched to said upper cup;

further comprising a water feed pipe and a cord arranged within the space of said diaper cup main body, said water feed pipe being connected to a private-parts wash nozzle and an anus wash nozzle installed in said upper cup, and said cord being connected to a feces-detecting sensor and a urine-detecting sensor installed in said upper cup;

wherein said upper cup of said diaper cup main body has a cavity formed in a surface of said upper cup on a side thereof to be fit on a pelvic region of a human body, said space being formed on a side of said upper cup opposite from said cavity, and an inner wall formed to join said lower cup, and said air blow port being formed at a plurality of positions in an upper end of said cavity; and wherein said upper cup of said diaper cup main body is formed with a first air blow port in a center of an upper end of said cavity, and second and third air blow ports in left and right positions relative to said first air blow port in the upper end of said cavity, and at least one guide wall positioned in said space to converge air flowing through the space.

5. A device for disposing excrement as claimed in claim 4, wherein said diaper cup main body has a flap covering said air blow ports on a side of said diaper cup main body to be fit on a pelvic region of a human body.

6. A device for disposing excrement as claimed in claim 5, wherein said diaper cup main body is formed arcuate in the upper end of said cavity, and said flap being formed generally arcuate and matched to a shape of the upper end of said cavity, said flap being fixed at a plurality of positions to thereby form an outlet port communicating to said air blow ports.

7. A device for disposing excrement as claimed in claim 6, wherein said flap is arranged in a slant surface of the upper end of said cavity of said diaper cup main body and screwed to said diaper cup main body in respective side portions of said air blow ports.

8. A device for disposing excrement as claimed in claim 7, wherein said diaper cup main body is continuously arranged with a waist-fit seat in the upper end, and said waist-fit seat has a support portion provided overlapping with said flap.

9. A device for disposing excrement as claimed in claim 8, wherein said waist-fit seat has a plate-like portion to be inserted in a bag provided in a changeable diaper, and a slant portion provided between said plate-like portion and said support portion and formed with a cutout groove.

10. A device for disposing excrement as claimed in claim 8, wherein said upper cup and said lower cup of said diaper cup main body are formed of a hard resin, and said flap and said waist-fit seat being formed of a resin that is softer than said upper cup and said lower cup and easy to bend and deform.

11. A device for disposing excrement as claimed in claim 5, wherein said diaper cup main body has a cup-washing nozzle on an inner side of said flap in a vicinity of said first air blow port to flow away excrement excreted by a sick person or the like.

12. A device for disposing excrement, comprising:

a diaper cup main body for enclosing a pelvic region of a human body, said diaper cup main body having an upper cup and a lower cup joined together with a space formed between said upper cup and said lower cup;

a cup-washing nozzle attached to an upper portion of said upper cup for spraying wash fluid into the upper cup, and a wash water feed pipe arranged within said space formed between said upper cup and said lower cup and connected to said cup-washing nozzle for supplying wash water to said nozzle;

an air blow port formed in the upper portion of said upper cup adjacent to said cup-washing nozzle, an air feed hose connected to said lower cup, and said space formed between said upper cup and said lower cup providing a passage for feeding air from said air feed hose to said air blow port;

an excrement suction hose connected to the upper cup for sucking wash water and excrement from a side of said upper cup facing a pelvic region of a human body; and a feces-detecting sensor and a urine-detecting sensor installed in said upper cup, and a cord arranged within said space formed between said upper cup and said lower cup and connected to said sensors.

13. The device for disposing excrement according to claim 12, wherein said air blow port comprises a plurality of air blow ports arranged in the upper portion of said upper cup, and said upper cup having at least one guide wall extending into said space for guiding air fed from said air feed hose into said air blow ports.

14. The device for disposing excrement according to claim 12, wherein said diaper cup main body has a flap attached to said upper cup which covers said air blow port and said cup-washing nozzle, said flap being arranged to direct the flow of air and wash water into a cavity of the upper cup.

* * * * *